United States Patent [19]

Poll et al.

[11] Patent Number: 4,909,941

[45] Date of Patent: Mar. 20, 1990

[54] HIGH PERFORMANCE LIQUID CHROMATOGRAPHY MOBILE PHASE

[76] Inventors: Dick J. Poll, Main Rd. R.D. 4; David R. K. Harding, 310 College Street, both of Palmerston North, New Zealand; William S. Hancock, 390 Robinwood La., Hillsborough, Calif. 94010

[21] Appl. No.: 281,548

[22] Filed: Dec. 8, 1988

Related U.S. Application Data

[63] Continuation-in-part of Ser. No. 876,792, Jun. 20, 1986.

[30] Foreign Application Priority Data

Jun. 24, 1985 [NZ] New Zealand ............... 212523

[51] Int. Cl.$^4$ .................................. B01D 15/08
[52] U.S. Cl. .................................. 210/635; 210/656; 210/542; 530/305; 530/371; 530/399; 530/417
[58] Field of Search ............... 530/305, 399, 413, 417, 530/371; 210/635, 656-659, 198.2, 198.3, 542

[56] References Cited

U.S. PATENT DOCUMENTS

| | | | |
|---|---|---|---|
| 3,907,676 | 9/1975 | Jorgensen | 530/417 |
| 4,073,725 | 2/1978 | Takeuchi | 210/279 |
| 4,122,094 | 10/1978 | Woziwodzki | 260/345.6 |
| 4,133,753 | 1/1979 | Takeuchi | 210/656 |
| 4,289,690 | 9/1981 | Pestka et al. | 424/85 |
| 4,377,482 | 3/1983 | Rivier | 210/635 |
| 4,447,328 | 5/1984 | Kamiyama | 210/656 |
| 4,485,017 | 11/1984 | Tan | 530/417 |
| 4,499,014 | 2/1985 | Estis | 530/351 |
| 4,500,431 | 2/1985 | Miyanaga | 210/656 |
| 4,525,465 | 6/1985 | Someno | 502/404 |
| 4,530,963 | 7/1985 | DeVoe | 210/679 |
| 4,533,494 | 8/1985 | Uchiyama et al. | 260/112.5 |
| 4,539,399 | 9/1985 | Armstrong | 536/103 |
| 4,549,965 | 10/1985 | Davis | 210/635 |
| 4,585,559 | 4/1986 | DeVoe | 210/679 |
| 4,599,175 | 7/1986 | Yamamizu | 210/656 |
| 4,626,416 | 12/1986 | Devoe | 210/682 |
| 4,666,604 | 5/1987 | Vijayalakshmi | 210/684 |
| 4,673,733 | 6/1987 | Chandra | 210/656 |

FOREIGN PATENT DOCUMENTS

| | | | |
|---|---|---|---|
| 102769 | 3/1984 | European Pat. Off. | 210/635 |
| 2616984 | 10/1977 | Fed. Rep. of Germany | 210/413 |
| 202207 | 10/1982 | New Zealand | 210/635 |

OTHER PUBLICATIONS

Regnier, Science, High Performance Liquid Chromatography of Biopolymers 222: 245-252, 1983.
Hancock, et al., HPLC Analysis of Biological Compounds-A Laboratory Guide, 1984.
Knighton, et al., Journal of Chromatography, 249:193-198, 1982.
Hancock, CRC Handbook of HPLC for the Separation of Amino Acids, Peptides and Proteins, II: 24,26,45, 1984.
Bishop et al., Journal of Liquid Chromatography, The Preparative Separation of Synthetic Peptides on Reversed-Phas Silica Packed in Radially Compressed Flexible-Willed Columns; 4(4):661-680, 1981.
Journal of Chromatography, Hancock, et al., Separation of Apolipproteins, 216:285-293, 1981.
Journal of Chromatography, Hancock, et al., Notes, 208:141-147, 1981.
Int. J. Peptide Protein Res., Hancock, et al., HPLC of PYR-HIS-GLY, 18:214-220, 1981.
Journal of Chromatography, Hancock, et al., Notes, 192:222-227, 1980.
McGraw-Hill Encyclopedia of Science & Technology vol. 3 at p. 104, McGraw-Hill Book Company, New York (1977).

*Primary Examiner*—Ernest G. Therkorn
*Attorney, Agent, or Firm*—Fleit, Jacobson, Cohn, Price, Holman & Stern

[57] ABSTRACT

There is described a mobile phase for use in the purification of proteins using reversed phase HPLC on a preparative scale. The mobile phase is an aqueous solution containing 0.005 to 1M of a physiologicially acceptable acid of the general formula YCOOH where Y is a polar electron withdrawing group capable of hydrogen bonding silanol groups. The solution also contains up to 95% by volume of a physiologically acceptable organic solvent. A preparative method of purifying proteins such as HSA or BSA and recombinant deoxyribonucleic proteins using reversed phased PHLC is also described.

4 Claims, 14 Drawing Sheets

TEST MIXTURE - CITRIC ACID

A. SUPELCO LC-3DP CA/KCl

B. WATERS 8 BMC 18 10µ CA/NaCl

C. SUPELCO LC-318 CA/KCl

D. WATERS NOVAPAK-C18 CA/NaCl

E. WATERS 8NVC 18 5µ CA/NaCl

F. VYDAC PROTEIN-C4 CA/NaCl

G. WHATMAN PROTESIL-300 OCTYL 25 CA/NaCl

H. SYNCHROPAK RP-P CA/NaCl

INSULINS, CITRIC ACID SYSTEM

A   LC-318 CITRIC ACID SYSTEM

B   LC-318 PHOSPHORIC ACID SYSTEM

C   LC-318 TFA SYSTEM

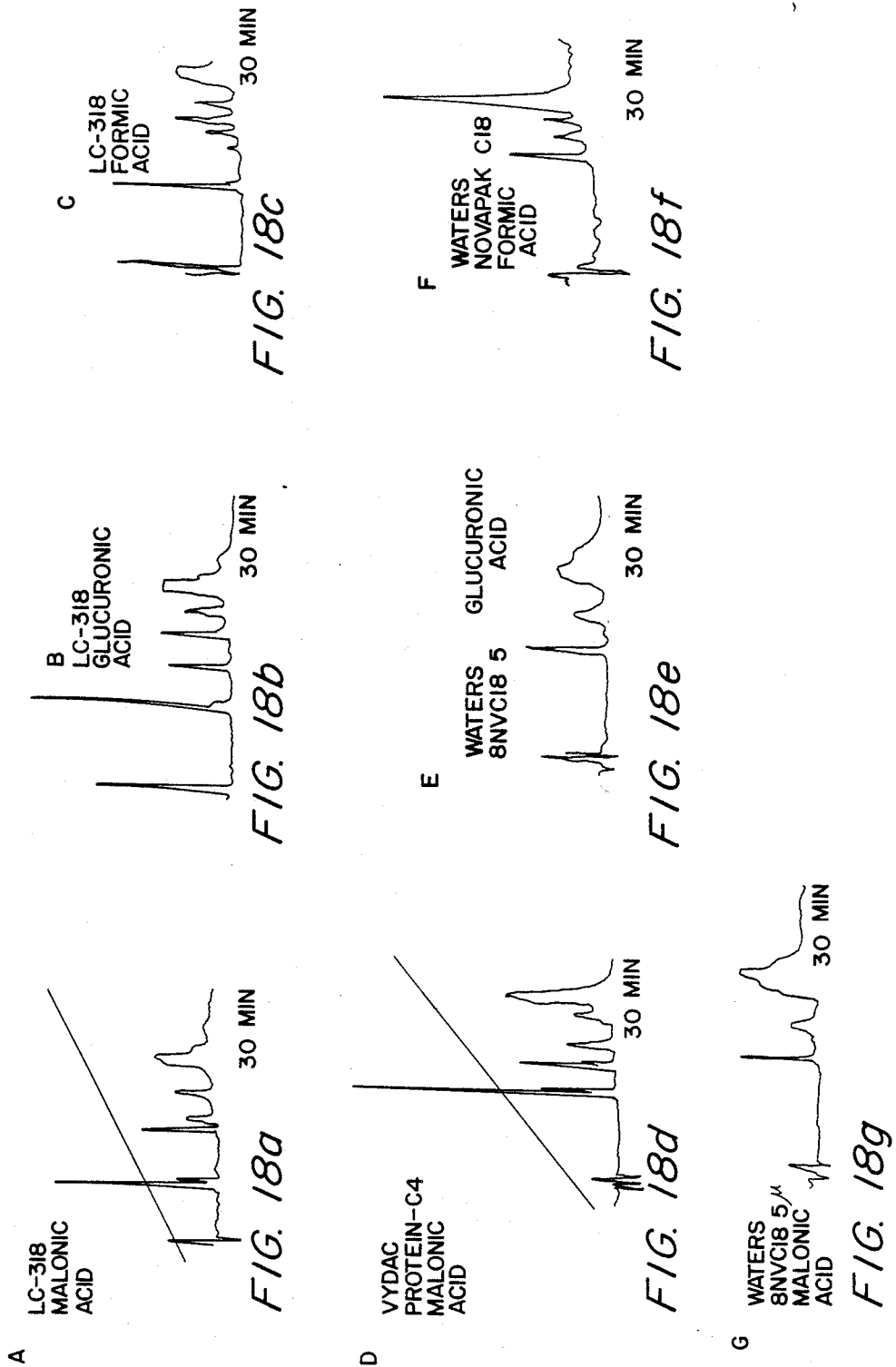

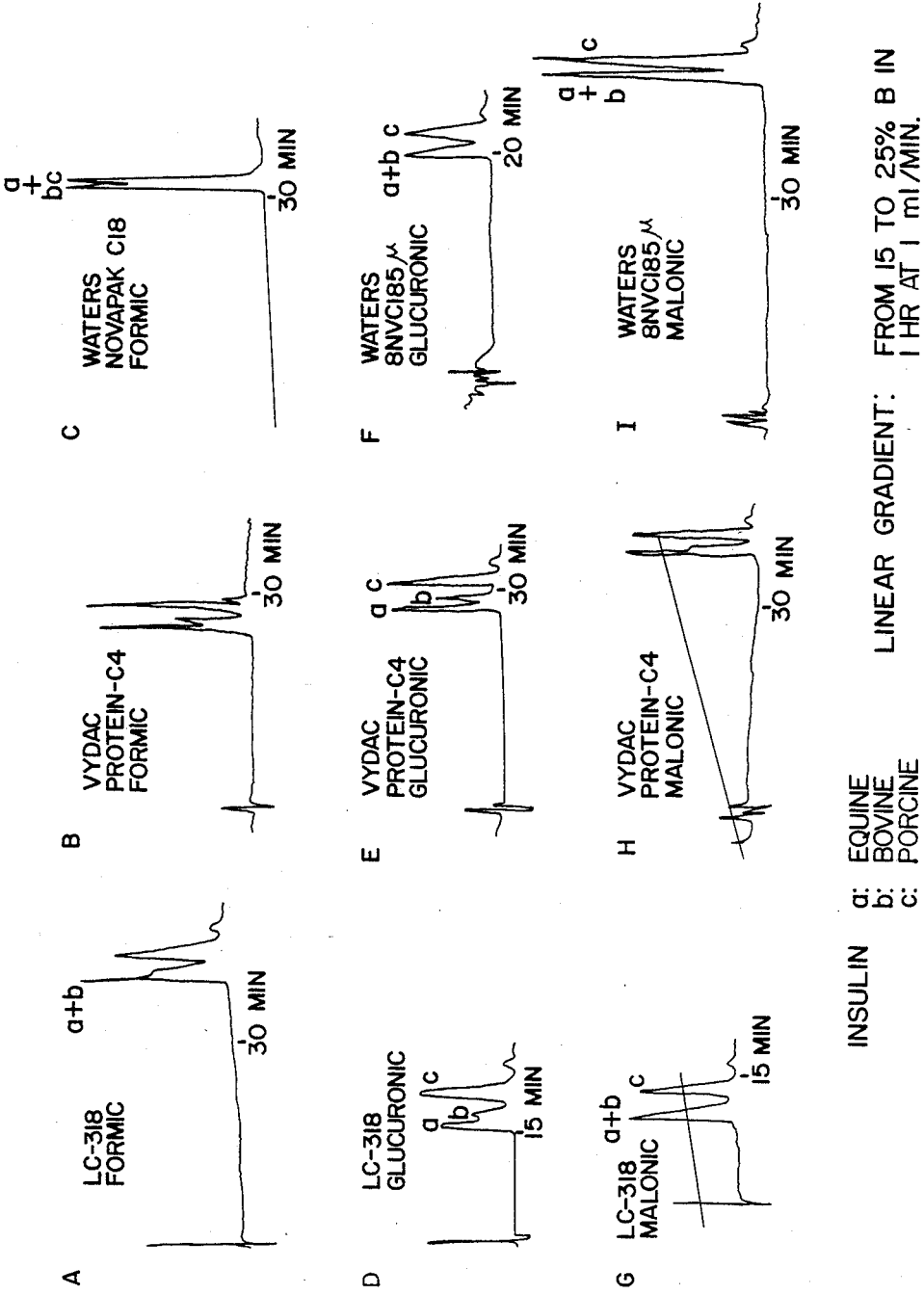

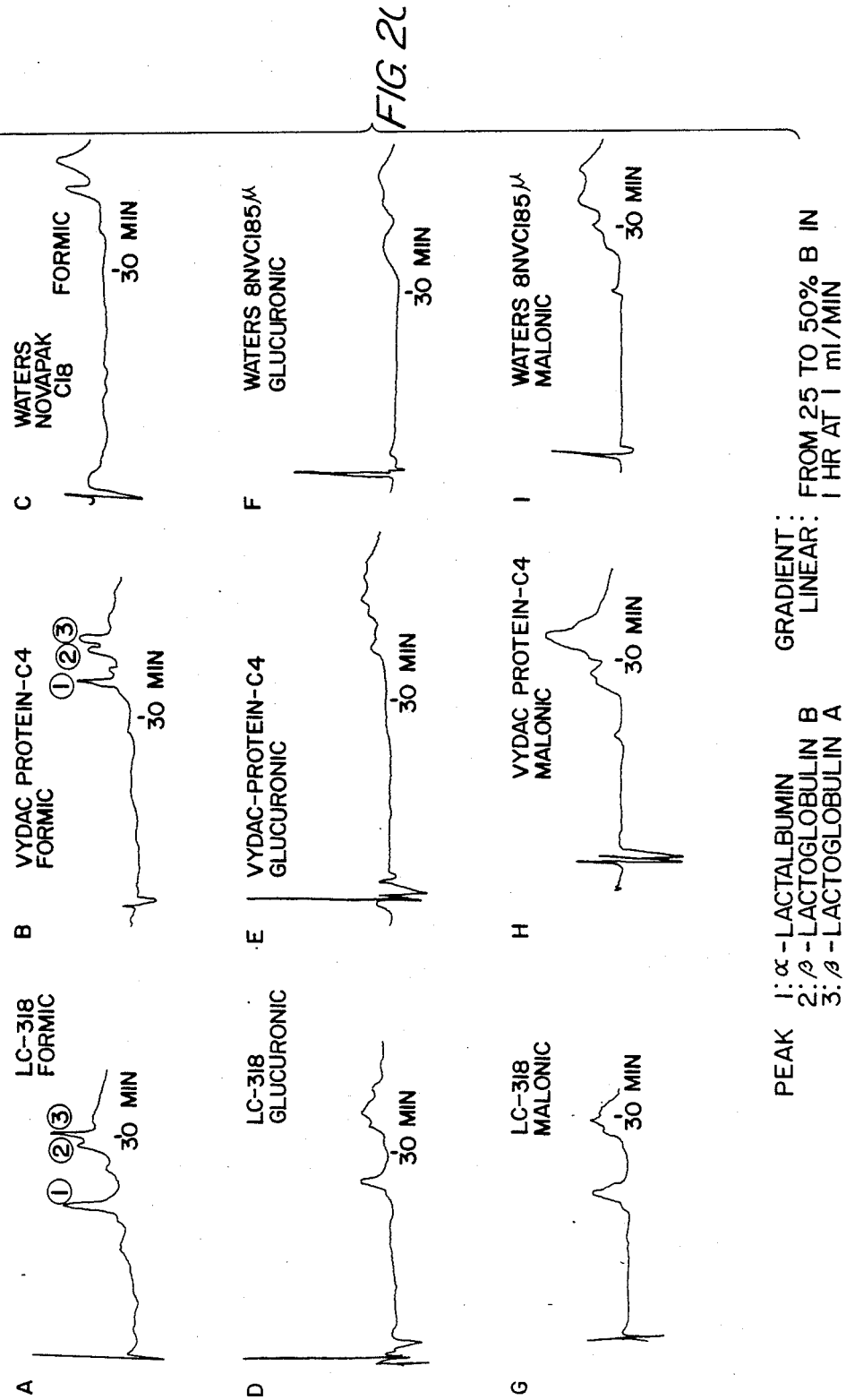

HIGH PERFORMANCE LIQUID CHROMATOGRAPHY MOBILE PHASE

CROSS-REFERENCE TO RELATED APPLICATIONS

This application makes reference to and claims the benefits available under 35 U.S.C. Section 120, of our application entitled, "High Performance Liquid Chromatography Mobile Phase" filed in the U.S. Patent and Trademark Office on June 20, 1986, and assigned Ser. No. 06/876,792, now abandoned.

FIELD OF INVENTION

This invention relates to high performance liquid chromatography (HPLC). More particularly, it relates to a mobile phase for use in reversed phase HPLC which is particularly suitable for the recovery of proteins.

BACKGROUND OF THE INVENTION

HPLC is established as an efficient tool in both analytical and preparative techniques for the recovery of biological products in high purity. Reversed HPLC with bonded supports (such as $C_{18}$-silica) is optimal for highly polar solutes. Reversed phase HPLC generally involves the use of a polar eluent with a non-polar support. Highly polar solutes have a greater affinity for the eluent than does the support and solutes are eluted in reverse order of polarity.

High molecular weight biological molecules such as proteins have a complex three dimensional structure which must be preserved to maintain the biological function of the sample. In a reversed phase chromatographic separation, the optimal separation involves the interaction between the hydrocabonateous groups of the support and hydrophobic surface features on column is therefore related to specific topological features of the individual protein species, with the components of lower or less accessible hydrophobic surface patches being eluted first. Because of this separation mechanism, HPLC is a highly resolutive chromatographic method. Even slight compositional differences between proteins will lead to topological differences which can result in an effective separation. For example, porcine and human insulin are easily separated by HPLC, although the two molecules only have a minor difference in a single amino acid residue.

Hydrophobic interactions between a target protein molecule and the reversed phase column must be carefully controlled. If the protein molecule is significantly destabilized in the chromatographic medium, unfolding of the three dimensional structure of the protein molecule can expose buried hydrophobic groups which can lead to additional hydrophobic interactions with the reversed phase column and prevent elution of the protein. Such increased interactions between the solute and stationary phase can lead to denaturation of the protein molecule and/or low recoveries due to irreversible multisite binding of the solute.

In addition, there are different requirements in conducting HPLC on a preparative scale from those in conducting HPLC on an analytical scale. The protein must not itself be denatured in a preparative process and it must not pick up any contaminants from either the mobile phase or the support at any time while it is passing through the column. Mobile phases used in analytical scale processes often destabilize the protein sample and thus are not suitable for preparative separations. In addition, solvents such as acetonitrile are widely used to elute polypeptide samples that are retained by reversed phase columns. Such solvents are highly toxic and cannot be used in preparative separations.

In reversed phase chromatography of proteins the solvents acetonitrile, isopropanol or propanol are used widely. Mixtures of phosphoric acid and amines and perfluorinated carboxylic acids, especially trifluoroacetic acid (TFA), are popular as ionic modifiers to be added to the mobile phase. While in analytical HPLC these solvents and buffer systems are acceptable, in preparative chromatography the solvents and ionic modifiers must be non-toxic and easily removed and some of the analytical reagents are not suitable for this reason.

The mobile phase for use in preparative HPLC should be mild to the protein so as not to denature it and be inert to the support. Damage to the support is not only inherently disadvantageous in relation to the support itself but can produce toxic by-products which are not acceptable with proteins which might be used for, for example, pharmaceutical applications.

OBJECTS OF THE INVENTION

It is an object of this invention to go some way towards avoiding these disadvantages or achieving these desiderata or at least to provide the public with a useful choice.

It is another object to provide an HPLC mobile phase process for isolating recombinant deoxyribonucleic acid proteins derived from complex mixtures of cell proteins.

It is still another object to provide an HPLC mobile phase process suitable for preparative scale uses.

It is yet another object to provide an HPLC mobile phase capable of producing proteins at enhanced levels of purity.

It is still yet another object to provide an HPLC mobile phase process capable of isolating proteins from complex mixtures.

It is a further object to provide an HPLC mobile phase process exhibiting superior resolving power.

It is a still further object to provide an HPLC mobile phase process capable of purification of protein pharmaceuticals derived from DNA.

It is a yet further object to provide an HPLC mobile phase process minimizing production of toxic by-products.

SUMMARY OF THE INVENTION

It has now been found unexpectedly, that the selection of a physiological carboxylic acid of structure YCOOH where Y is a polar electron withdrawing group capable of hydrogen bonding silanol groups in a siliconaceous support, goes some way to achieving these desiderata. A preferred physiological carboxylic acid is a carboxylic acid which is present in vivo in a biochemical pathway such as the glycolytic pathway or the citric acid cycle. Not only are these acids of a natural origin and thus suitable in pharmaceutical applications, but unexpectedly these acids allow stabilization of the native protein structure (so as to control the undesired interactions between the support phase and the solute) as well as allowing elution of the protein sample under milder chromatographic conditions. Because of the stabilization of protein structure (and thereby limiting the number of hydrophobic contacts with the reversed phase) a lower concentration of organic solvent or a solvent of lower elutrophic strength can be used to elute the protein molecule.

Thus, this invention allows the use of ethanol in a mobile phases with subsequent advantages in pharmaceutical applications. Ethanol is not sufficiently non-polar to elute protein samples which have a high number of non-polar interactions with the support phase. This invention also allows the use of a moderate pH <2.2 or pH >5 which are currently used in reversed phase chromatography of proteins. The use of moderate pH values results in greater stability of both the protein sample and the stationary phase. Therefore, the purified protein is recovered with higher biological activity and is not contaminated with $C_{18}$-silica or other degradation products caused by hydrolysis of the $C_{18}$-silica with either the high or low pH values.

Another unexpected advantage of this invention is that the physiological carboxylic acid of structure YCOOH associates via hydrogen bonding interactions with silanol groups of the reversed phase column. These interactions result in a dynamic layer of physiological acid being associated with the underlying silica and thereby prevent a direct interaction between the ammonium groups of protein molecules and the silanol groups present in the reversed phase packing material. These undesired interactions have been associated with loss of protein materials by irreversible binding and with peak broadening and tailing with consequent losses of separate efficiency.

The application of reversed phase HPLC to the purification of protein pharmaceuticals derived from recombinant deoxyribonucleic acid (rDNA) techniques is particularly important due to the very high levels of purity required by the Food and Drug Administration (FDA) before licensing approval. Typically, the FDA requires a level of host cell contamination no greater than 100 parts per million and a level of rDNA protein variants no greater than 1%. The reason for the requirement of such high purity levels is that genetic engineering has greater potential risks than the well established technologies used in the isolation of proteins from traditional sources such as human serum albumin from human plasma samples. rDNA proteins must be isolated from complex mixtures of many cell proteins which may well have much greater toxicity than mammalian protein mixtures. One example is the toxicity of E. coli proteins which in very low levels (μg/kg) can cause potent side effects. Harmful by-products include bacterial endotoxins and oncogenes.

Therefore, the superior resolving power of reversed phase HPLC is particularly well suited to the purification of rDNA derived proteins. Recombinant DNA derived proteins are being used in pharmaceutical applications. Thus, the use of a physiologically acceptable mobile phase allows the isolation of the highly purified protein without introducing toxic buffer components in preparative scale separations.

Accordingly, the invention may be said broadly to consist in a solution suitable for use as a mobile phase in preparative HPLC which comprises substantially pure water containing 0.005 to 1 molar of physiologically acceptable carboxylic acid, the acid being of the general formula YCOOH wherein Y is a polar electron withdrawing group capable of hydrogen bonding silanol groups in a siliconaceous support, said solution also containing up to 95% by volume of a physiologically acceptable organic solvent.

Preferably Y is H, $X(CR_1R_2)n—$, or a cyclic or heterocyclic ring compound substituted with hydroxy groups, wherein, X is —H, —OH, —COOH; $R_1$ and $R_2$ (which may be the same or different) are —H, —OH, —COOH; or —$R_3$COOH wherein $R_3$ is lower alkyl; and n is 0 or an integer from 1 to 5.

Preferably said carboxylic acid is selected from the group consisting of malonic acid, citric acid, galacturonic acid, galucuronic acid or formic acid.

Preferably the solution contains a salt selected from the group consisting of NaCl, KCl, and $NH_4Cl$.

Most preferably said carboxylic acid is selected from the group consisting of citric acid and formic acid.

Preferably said organic solvent is ethanol.

Alternatively said organic solvent is selected from the group consisting of methanol, propanol or isopropanol.

The invention may also be said broadly to consist in a method of purifying on a preparative scale a recombinant deoxyribonucleic acid protein derived from a mixture thereof with cell proteins by reversed phase HPLC which comprises the steps of:

providing a column packed with an HPLC support of sufficient porosity to allow passage of proteins therethrough, introducing a recombinant deoxyribonucleic acid protein derived from a mixture thereof with cell proteins into the end of said column, and eluting said column with a mobile phase comprising substantially pure water containing .055 to 1 molar of a physiologically acceptable carboxylic acid, the acid being of the general formula YCOOH wherein Y is a polar electron withdrawing group capable of hydrogen bonding silanol groups in a silicarbonaceous support, said solution also containing from 10.5% up to 95% by volume of a physiologically acceptable organic solvent.

Preferably in said mobile phase said physiologically acceptable carboxylic acid is citric acid and said organic solvent is ethanol.

Preferably said method includes the subsequent step of isolating said recombinant protein by a method selected from the group consisting of ultra-filtration and dialysis.

Preferably said recombinant protein is selected from the group consisting of recombinant human growth hormone and recombinant human insulin.

BRIEF DESCRIPTION OF THE DRAWINGS

The invention may be more fully understood by having reference to the accompanying drawings in which FIGS. 1–23 are chromatograms of the following substances and under the following conditions:

| FIG. 1: | COLUMN: Partisil 10 ODS (300 × 4 mm) |
|---|---|
| | Buffers |
| | (A) 0.1% citric acid in $H_2O$/2-Propanol (9:1) (B) 0.1% citric acid in $H_2O$/2-Propanol (1:9) Linear gradient from 0 to 100% in 1 hour at 1 ml/min. Detector: Waters Model 450 variable wave length detector at 220 nm. A 2.0 CHART: 200 mm/hr Insulin (porcine) retention time = 17–18 |

-continued

Figure 1:
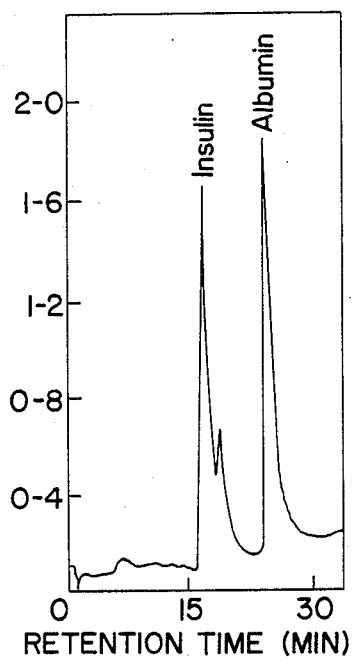
Figure 2:
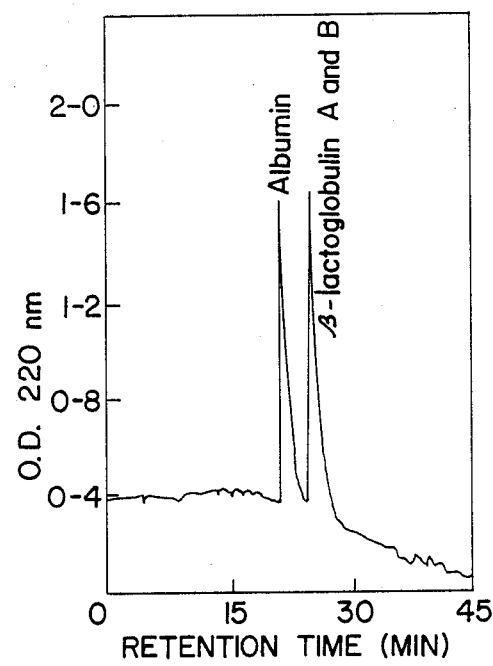

| | |
|---|---|
| | min.<br>Albumin (bovine)<br>retention time = 25-27 min. |
| FIG. 2 | COLUMN: Rad-Pak = $C_{18}$<br>Buffers: (As in FIG. 1)<br>Linear gradient from 0 to 100% in 1 hour at ml/min.<br>Detention: 280 nm A 0.1<br>Chart: 200 mm/hr<br>Albumin (bovine)<br>β-lactoglobulin (A)<br>β-lactoglobulin (B) not separated |
| FIG. 3a | Instrument: Prep/LC-500 (Waters)<br>Column: Prep-Pak-$C_{18}$ (1 cartridge)<br>Buffers:<br>(A) 0.1% 1% citric acid $H_2O$/95% EtOH (9:1) 3 liters<br>(B) 0.1% citric acid in $H_2O$/95% EtOH (1:9) 3 liters<br>Gradient concave at 50 ml/min.<br>Detection: 280 nm; A 1.0 and 2.0 (see chart)<br>CHART: 200 mm/hr<br>1.0 g of insulin (porcine; Nordisk)<br>retention time 65 min. |
| FIG. 3b: | Insulin after chromatography on the Prep/LC-500 (see 3a)<br>Column: Rad-Pak-$C_{18}$<br>Buffers:<br>(A) 0.1% citric acid in $H_2O$/2-Propanol (9:1) (B) 0.1% citric acid in $H_2O$/2-Propanol (1:9)<br>Gradient: linear from 0 to 100% at 1 ml/min. in 1 hour<br>Detection: 220 nm A 2.0<br>125 μg of insulin.<br>Retention time 23 min. |
| FIG. 4: | Instrument: Prep/LC-500 Waters.<br>1.0 g bovine serum albumin (BSA)<br>COLUMN: Prep-Pak-$C_{18}$ (1 cartridge)<br>Buffers:<br>(A) 0.1% citric acid in $H_2O$/95% EtOH (9:1) 2 liters<br>(B) 0.1% citric acid in $H_2O$/95% EtOH (1:9) 3 liters<br>Gradient: concave at 50 ml/min<br>Detection: 280 nm A 2.0<br>Chart: 200 mm/hr<br>Retention time 85 min (top of peak) |
| FIG. 5: | COLUMN: Rad-Pak-$C_{18}$<br>Buffers:<br>(A) 0.1% citric acid in $H_2O$/2-Propanol (9:1) (B) 0.1% citric acid in $H_2O$/2-Propanol (1:9)<br>Detection: 220 nm<br>Insulin (porcine: Nordisk) 50 μg<br>Albumin (bovine: Sigma) 50 μg<br>β-Lactoglobulin A 50 μg<br>β-Lactoglobulin B 50 μg |

-continued

Figure 5:
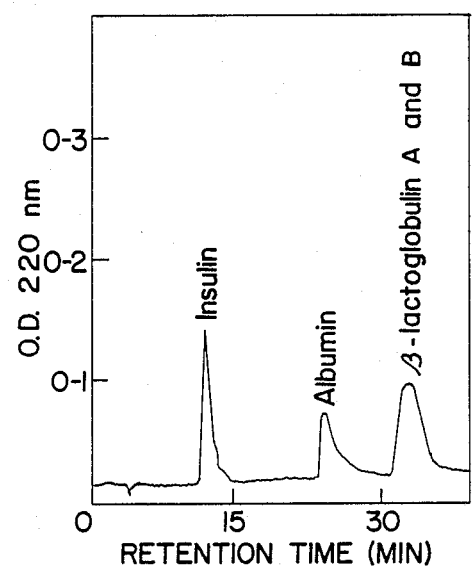
Figure 6:
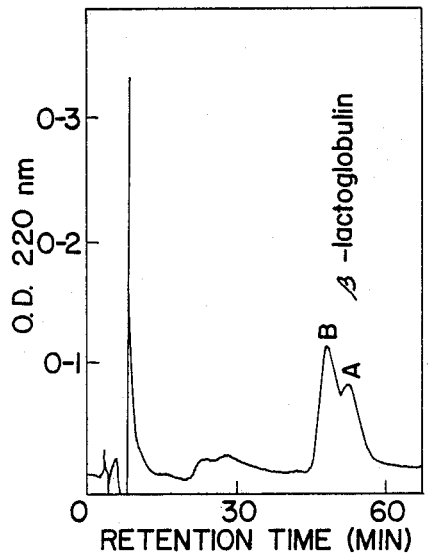
Figure 9:
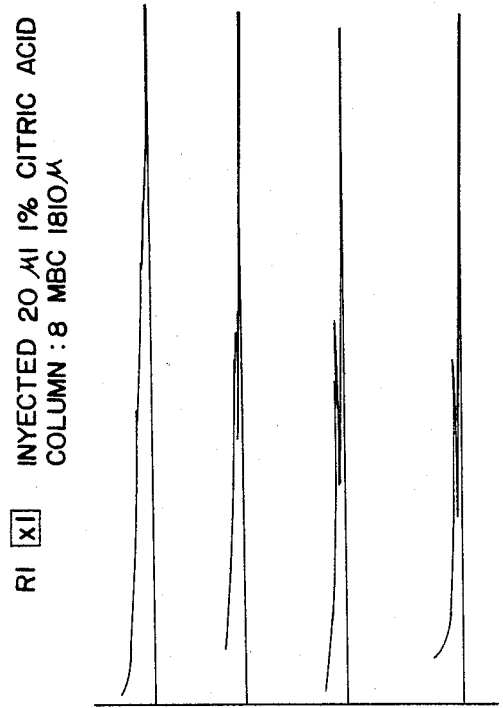
Figure 10:
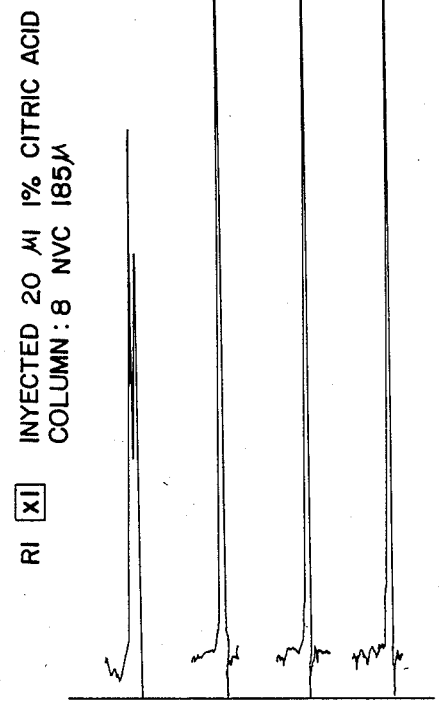
Figure 11A:
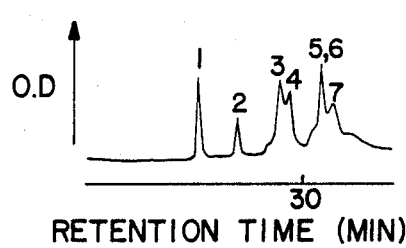
Figure 11B:
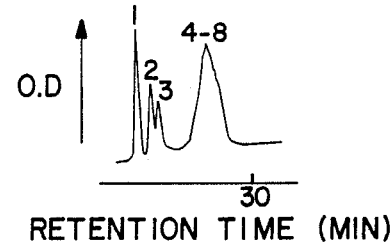
Figure 11C:
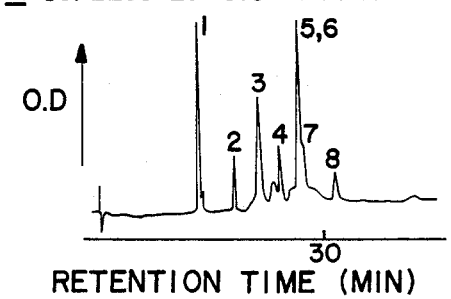
Figure 11D:
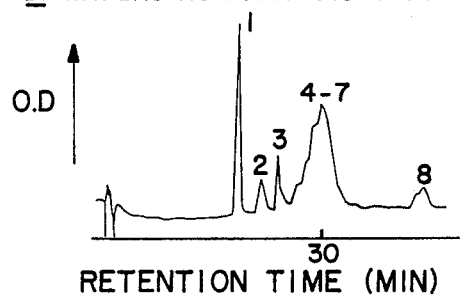
Figure 11E:
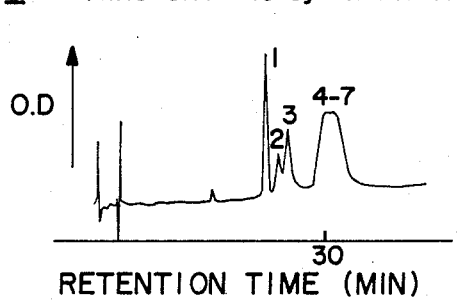
Figure 11F:
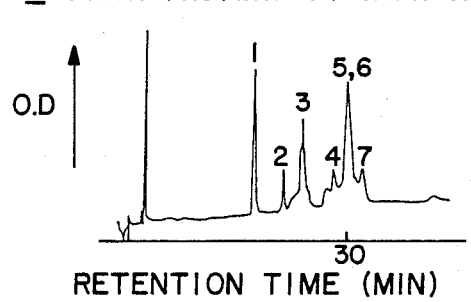
Figure 11G:
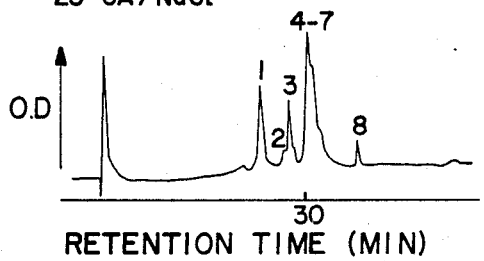
Figure 11H:
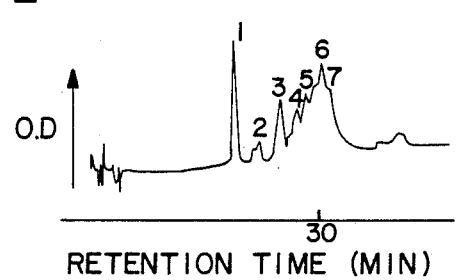
Figure 12A:
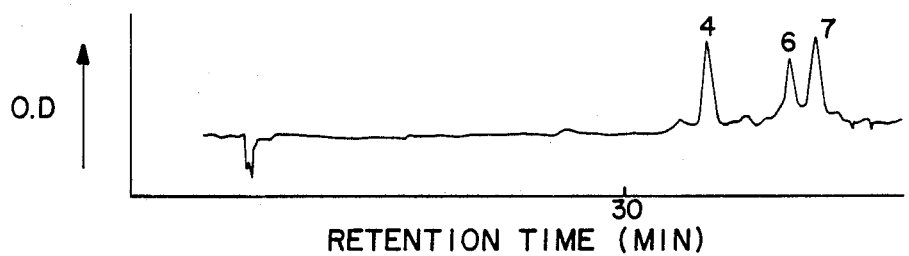
Figure 12B:
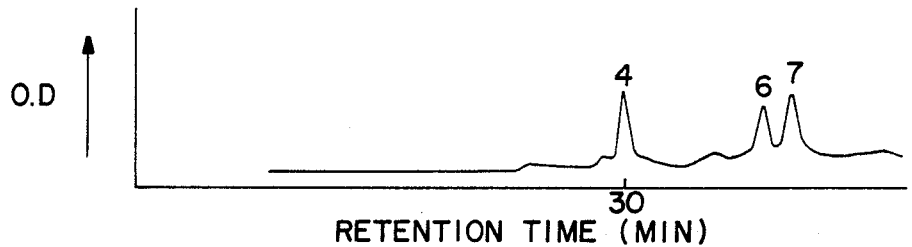
Figure 12C:
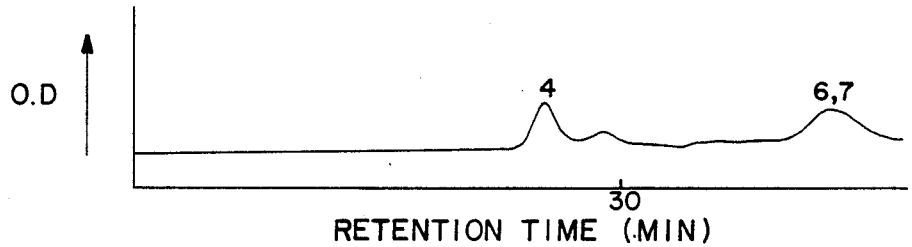
Figure 12D:
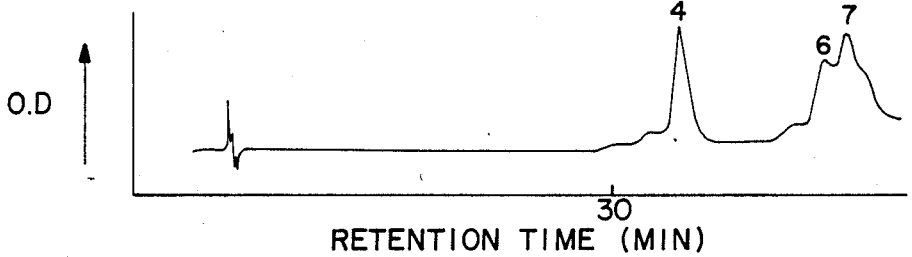
Figure 13A:
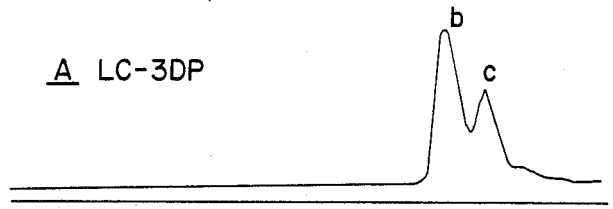
Figure 13B:
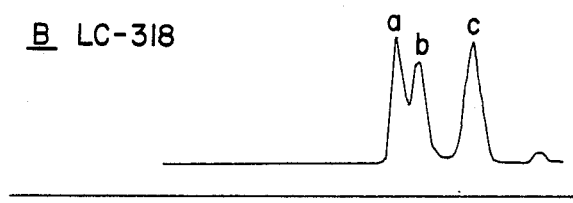
Figure 13C:
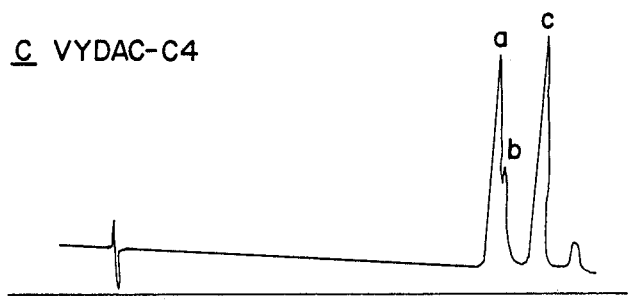
Figure 13D:
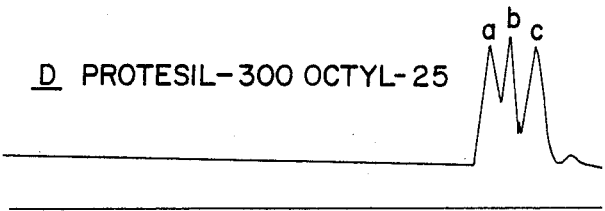

| | |
|---|---|
| | Detection: 280 nm A 2.0<br>Chart: 200 mm/hr |
| FIG. 6: | Conditions as in FIG. 5<br>β-Lactoglobulin A 50 μg<br>β-Lactoglobulin B 50 μg<br>Detection: 280 nm A 2.0<br>Chart: 100 mm/hr<br>Gradient: Linear from 25 to 50% in 1 hour at 0.5 ml/min. |
| FIG. 7: | Conditions as in FIG. 6<br>100 μg of whey protein |
| FIG. 8a: | The separation of human growth hormone, Nordisk Insulin Laboratories.<br>Conditions as in FIG. 5.<br>GRADIENT: Linear 25 to 100% in 1.5 hr. at 0.5 ml/min. |
| FIG. 8b: | The separation of human growth hormone. New Zealand National Hormone Laboratory.<br>Conditions as in FIG. 5<br>GRADIENT: Linear 25 to 50% in 1 hr. at 0.5 ml/min. |
| FIG. 9: | Coating of the column with acid.<br>Column: Waters; 8 MBC1810 μ, P4194A01<br>Solvent:<br>water/2-propanol 9:1<br>Injections (repeated) of 1% (v/v) citric acid. (20 μl)<br>Detection: Differential Refractometer R401<br>Sensitivity X 2. |
| FIG. 10: | Column: Waters; 8NVC18 5μ, P4136DO1<br>Solvent:<br>water/2-propanol 9:1<br>Injection of 1% citric acid (20 μl)<br>Detection: R 401 sensitivity X1 |
| FIG. 11: | Shows a test mixture of proteins on 8 different columns.<br>COLUMN A: SUPELCO: LC-3DP<br>COLUMN B: WATERS: 8MBC1810 μ<br>COLUMN C: SUPELCO: LC-318<br>COLUMN D: WATERS: NOVPAK-C18<br>COLUMN E: WATERS: 8NVC185 μ<br>COLUMN F: VYDAC: PROTEIN-C4<br>COLUMN G: WHATMAN: PROTESIL-300 OCTYL-25<br>COLUMN H: SYNCHROM. INC.: SYNCHROPAK RP-P<br>Buffer: citric acid/salt system<br>Program: Linear gradient usually from 15–100% B in 1 hour at 1 ml/min.<br>Sample: peak 1: insulin (porcine)<br>peak 2: cytochrome C. (horse heart)<br>peak 3: bovine serum albumin<br>peak 4: α-lactalbumin |

| | -continued | |
|---|---|---|
| | peak 5: (+8): myoglobin (equine skeletal muscle) peak 6: β-lactoglobulin B peak 7: β-lactoglobulin A | |
| FIGS. 12A–12D: | Separation of whey proteins. Mixture containing: peak 4: α-lactalbumin 6: β-lactoglobulin B 7: β-lactoglobulin A | |
| | Columns: A VYDAC: C4 B SUPELCO: LC-318 C SUPELCO: LC-3DP D SYNCHROM. INC.: SYNCHROPAK RP-P Buffer: citric acid system Program: linear gradient from 25–50% B in 1 hour at 1 ml/min. | |
| FIGS. 13A–13D | Separation of insulins. Buffer: citric acid system Program: linear gradient from 13–20% B (column A) linear gradient from 15–25% B (others) in 1 hour at 1 ml/min. Sample: peak (A) equine insulin (B) bovine insulin (C) porcine insulin Columns used: A SUPELCO: LC-3DP B SUPELCO: LC-318 C VYDAC: PROTEIN-C4 D PROTESIL - 300 OCTYL-25 | |
| FIG. 14: | Preparative chromatography of 1.0 g of bovine serum albumin. Instrument: Prep-500 Waters Column: 1 C18 - cartridge Buffers: A: 0.1% citric acid + 1% NaCl in $H_2O/95\%$ EtOH 3:1 Buffer B: 0.1% citric acid + 1% NaCl in $H_2O/95\%$ EtOH 45:55 Gradient was concave and was made up from 1 liter buffer A and 5 l liter buffer B. | |
| FIGS. 15 (a–c) | On the Supelco LC-318 column was injected the general test mixture described before. Buffers: | |
| FIG. 15a: | A: 0.1% citric acid + 1% salt in $H_2O$/IPA 9:1 B: 0.1% citric acid + 1% salt in $H_2O$/IPA 1:4 | |
| FIG. 15b: | A: 0.1% v/v $H_3PO_4$ + 1% salt in $H_2O$/IPA 9:1 B: 0.1% v/v $H_3PO_4$ + 1% salt in $H_2O$/IPA 1:4 | |
| FIG. 15c: | A: 0.1% TFA + 1% salt in $H_2O$/IPA 9:1 B: 0.1% TFA + 1% salt in $H_2O$/IPA 1:4 Linear gradients from 15–60% in 1 hour at 1 | |

Figure 15A:
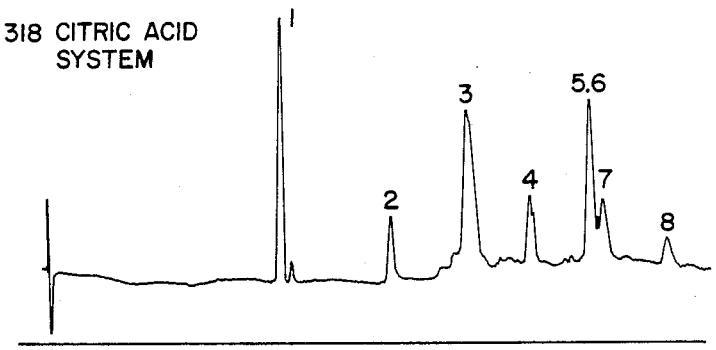
Figure 16A:
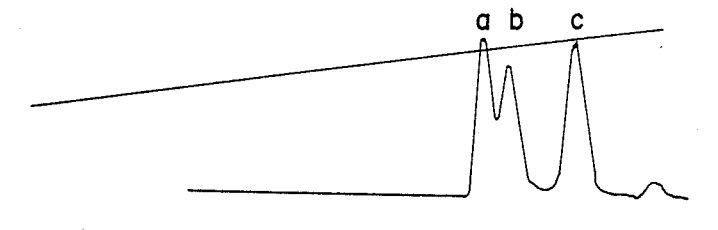
Figure 16B:
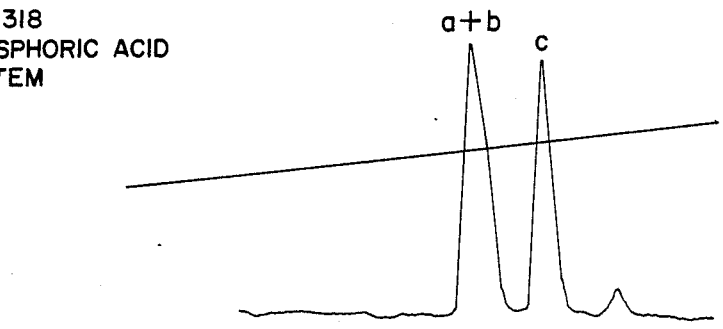
Figure 16C:
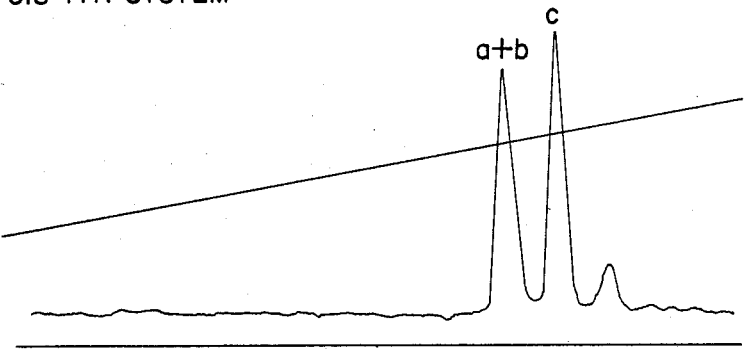
Figure 17A:
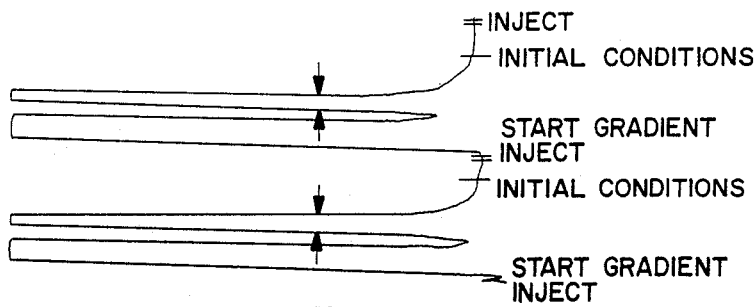
Figure 21:
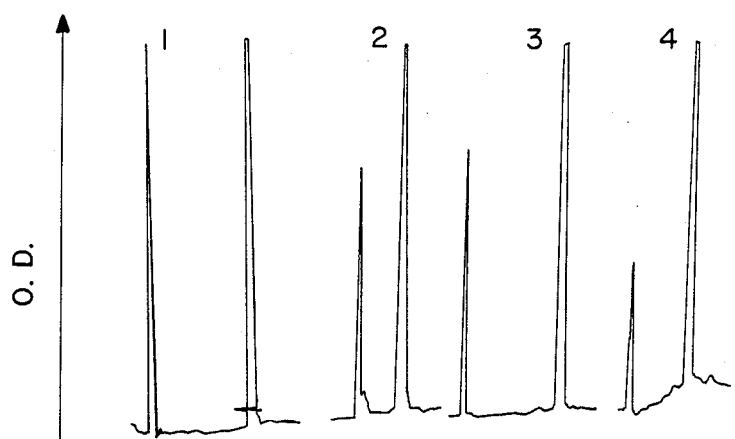
Figure 22:
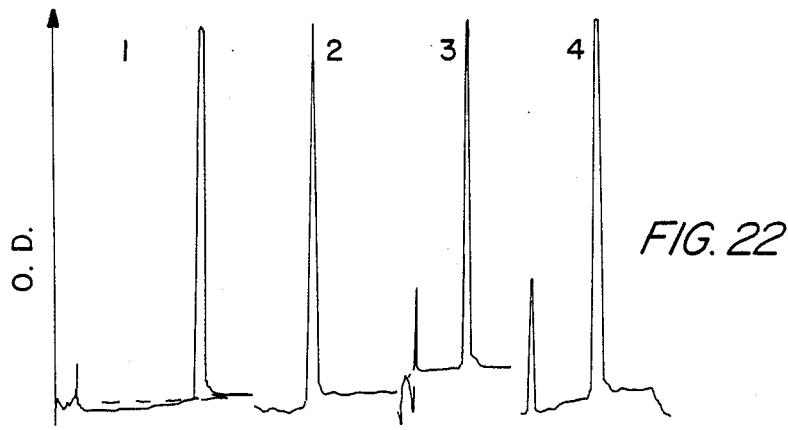

| | -continued | |
|---|---|---|
| | ml/min. for A and B From 5–60% B in 1 hour ml/min. for C. | |
| FIGS. 16A–16c | On the Supelco LC-318 column was injected a mixture of: (a) equine insulin (b) bovine insulin (c) porcine insulin Buffers as in FIG. 15a Gradients: A and B from 15–25% B in 1 hour; 1 ml/min. C from 10–25% B in 1 hour; 1 ml/min. | |
| FIG. 17: | On a Synchroprep column was injected: A. Human Serum Albumin (HSA) B. Bovine Serum Albumin (BSA) C. Porcine Insulin. Other parameters are set out in Example 11 | |
| FIG. 18: | On the columns listed a general protein mixture was injected. Other parameters are set out in Example 12. | |
| FIG. 19: | As in FIG. 18 except insulins were injected as exemplified in Example 12. | |
| FIG. 20: | As in FIG. 18 except whey proteins were injected as exemplified in Example 12. | |
| FIG. 21: | Column Synchropak RP-P Sample: 5 mg of rhGH Buffers: System 1: Buffer A: 0.1% TFA in $H_2O/CH_3CN$ 9:1 Buffer B: 0.1% TFA in $H_2O/CH_3CN$ 1:4 System 2: Buffer A: 0.1% $H_3PO_4$ + 1% NaCl in $H_2O/CH_3CN$ 9:1 Buffer B: 0.1% $H_3PO_4$ + 1% NaCl in $H_2O/CH_3CN$ 1:4 System 3: Buffer A: 0.1% citric acid + 1% guanidine.HCl in $H_2O/CH_3CN$ 9:1 Buffer B 0.1% citric acid + 1% guanidine.HCl in $H_2O/CH_3CN$ 1:4 | |
| FIG. 22: | Column: As in FIG. 21 Sample: 5 mg of met.hGH Buffers: As in FIG. 21 | |
| FIG. 23: | Column: As in FIG. 21 Sample: 2 ml of recombinant human insulin Buffers: As in FIG. 21, system 4. | |

DETAILED DESCRIPTION OF THE PREFERRED EMBODIMENTS

HPLC was carried out according to the techniques described in the following references:
1. *Journal of Chromatography* 192 (1980) 222–227.
2. *Journal of Liquid Chromatography* 4,661–680 (1981).
3. *Journal of Chromatography* 249 (1982) 193–198.

In addition to the $C_{18}$-silica columns used in these papers, it is also possible to use, for example, alkylphenyl or $C_8$ columns.

In examples 1 and 2, insulin and serum albumin were examined as examples of small and large proteins respectively. The separation of albumin was found to be much more demanding than insulin. Only the superior eluotrophic properties of the ionic modifiers of the formula YCOOH allowed good recovery and separation of albumin in the presence of ethanol-water mixtures. Example 8 shows that the nature of the gradient of organic solvent is important.

EXAMPLE 1: Testing of Buffer Systems

Gradient systems were set up starting with water/isopropanol 9:1 and ending at 1:9 to which was added 0.1% acid (Tables 1 and 2). Compounds marked with + + did not only allow elution of the protein but the peak shape and recoveries were good.

The gradient was delivered by two Waters HPLC pumps Model 6000 A in combination with a Model 660 solvent programmer.

Detection: Waters Model 450 Variable Wavelength Detector at 220 mm and 2.0 Aufs.

Column: $C_{18}$-Radial Pak, 8 mm i.d. (8MBC1810μ; P3171D02)

Buffer A: 0.1% reagent in water/isopropanol 9:1
Buffer B: 0.1% reagent in water/isopropanol 1:9

Solvents were freshly prepared and filtered through Millipore filters. (0.45 μm).

100 μg of bovine albumin (Sigma, No. A-4503) was injected in a linear gradient run from Buffer A to B in one hour at 1.0 ml/min.

The strong inorganic acids, hydrochloric and sulphuric were tested in a different way using small glass columns filled with $C_{18}$-silica (37-75μ). Albumin was eluted but damage to the columns was evident, as shown by the elution of the waxy $C_{18}$-column coating.

TABLE 1

| Acids | pKa$_1$ | pH of Buffer A | Elution of Albumin | Remarks |
|---|---|---|---|---|
| Hydrochloric | | | + | |
| Sulphuric | | | + | strong acids damaging to $C_{18}$-column |
| TFA | 0.30 | 2.15 | | |
| Oxalic | 1.23 | 2.23 | + | |
| Maleic | 1.83 | 2.38 | − | |
| Phosphoric | 2.12 | 2.57 | + | |
| Malonic | 2.83 | 2.57 | + + | |
| Tartaric* | 2.98 | 2.75 | + | Peak shape bad |
| Glucuronic | 3.00 | 2.75 | + | |
| Fumaric | 3.03 | 2.75 | − | |
| Lactic | 3.08 | 2.86 | + | Peak shape bad |
| Citric | 3.14 | 3.00 | + + | |
| Galacturonic ~ | 3.5 | 3.30 | + + | |
| Formic | 3.75 | 3.30 | + + | |
| Glycolic | 3.83 | 3.14 | + | Peak shape bad |
| Ascorbic | 4.10 | 3.40 | − | |
| Succinic | 4.16 | 5.10 | + | Less then 0.1% used because of poor solubility. Peak shape bad |
| Acetic | 4.75 | 3.40 | + | Peak shape bad |

*TARTARIC ACID MUST NOT BE USED WITH NaCl as there is a strong tendency for sodium hydrogen tartrate to crystallise on column, in pumps and samples etc.

TABLE 2

| Acids | PKa$_1$ | pH of Buffer A | Elution of Insulin | Remarks |
|---|---|---|---|---|
| Hydrochloric | | | + | |
| Sulphuric | | | + | strong acids damaging to $C_{18}$-column |
| TFA | | 2.15 | + | |
| Oxalic | 1.23 | 2.23 | + | |
| Maleic | 1.83 | 2.38 | − | |
| Phosphoric | 2.12 | 2.57 | + | |
| Malonic | 2.83 | 2.57 | + + | |
| Tartaric* | 2.98 | 2.75 | + | Peak shape bad |
| Glucuronic | 3.00 | 2.75 | + | |
| Fumaric | 3.03 | 2.75 | − | |
| Lactic | 3.08 | 2.86 | + | Peak shape bad |
| Citric | 3.14 | 3.00 | + + | |
| Galacturonic ~ | 3.5 | 3.30 | + + | |
| Formic | 3.75 | 3.30 | + + | |
| Glycolic | 3.83 | 3.14 | + | |
| Ascorbic | 4.10 | 3.40 | − | |
| Succinic* | 4.16 | 5.30 | + | *Saturated solution <0.1% Peak shape bad |
| Acetic | 4.75 | 3.40 | + | Peak shape bad |

*TARTARIC ACID MUST NOT BE USED WITH NaCl as there is a strong tendency for sodium hydrogen tartrate to crystallise on column, in pumps and samples etc.

EXAMPLE 2: Preparative Scale Purification of Albumin (citric acid)

Instrument: Prep LC/System 500 A (Waters)
Detection: Model 550 A Variable Wavelength Detector at
280 n m; A 2.0 (Waters)
Column: 1 $C_{18}$-silica cartridge
Buffer A: 0.1% citric acid in water/95% ethanol 9:1 (2.2 1)
Buffer B: 0.1% citric acid in water/95% ethanol 1:9 (3 1)

The concave gradient was obtained by a simple mixing flask containing buffer A. This flask is closed with a rubber bung through which one TEFLON ® tube leads to the chromatograph, the other to buffer B. Buffer B automatically flows into this mixing flask when the pump is running.

The albumin sample (1.0 gram) is dissolved in 200 ml of water and pumped onto the column, the system is washed with 200 ml of buffer A after which the gradient is started.

Figure 3A:
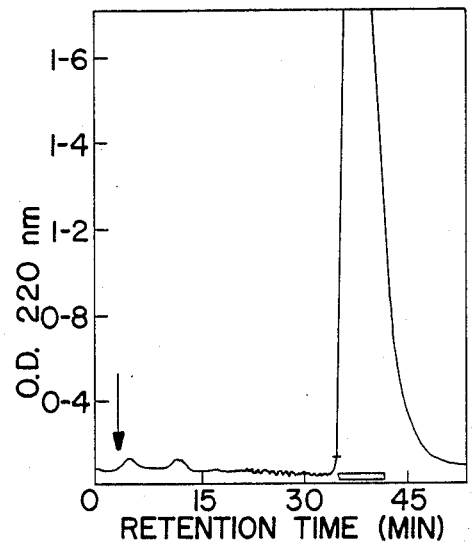

Albumin is eluted after about 1.5 1 of buffer has been used and at this moment the ratio of alcohol/water is approximately 1:1 (FIG. 3a).

Working Up Procedure

The albumin solution obtained above is diluted to about 20% alcohol and subjected to ultrafiltration. By this technique the buffer components are removed. Subsequently, the albumin may be freeze dried to a colorless powder. Alternatively, the albumin solution can be adjusted to a desirable buffer composition for direct use.

EXAMPLE 3: Preparation of Semi-Purified Insulin

Insulin may be treated by the method set out in Example 2 of United Kingdom Patent Specification No. 1,285,024 except that the ion exchanger to be used is INDION-QAE ®. This is a strongly basic ion exchanger whose functional group is quaternary amine and whose counter ion is chloride. It is a cross-linked hydrophilic matrix derived from regenerated cellulose. INDION-QAE is a registered trademark of Phoenix Chemicals Limited, C/o Waitaki NZ Refrigerating Limited, P.O. Box 1472, Christchurch, New Zealand.

EXAMPLE 4: Other Separations of Proteins

In general, a gradient was used from initial buffer A (0.1% citric acid in water and 2-propanol ratio 9:1) to buffer B (0.1% citric acid in water and 2-propanol-ratio 1:9).

Note: In these examples, the citric acid concentration is constant throughout the gradient. The results of these separations are shown in the accompanying drawings as discussed below.

FIGS. 1 and 2 show separation of porcine insulin from bovine albumin and albumin from $\beta$-lactoglobulin A and B respectively.

FIG. 3a shows a preparative chromatography run (Prep. 500) of porcine insulin (1 gram) with citric acid-ethanol system (see example 1).

Figure 3B:
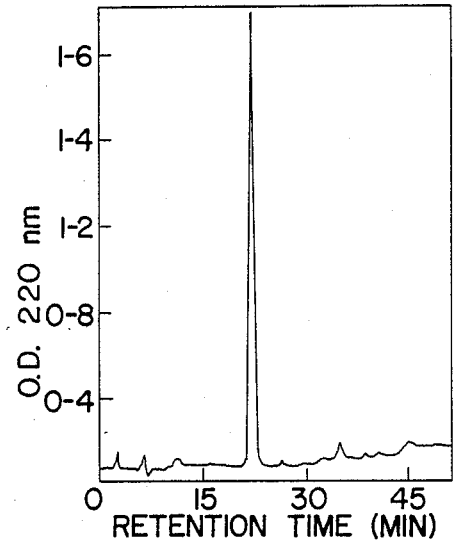

FIG. 3b is the analytical chromatogram of the preparative run in 3a.

Figure 4:
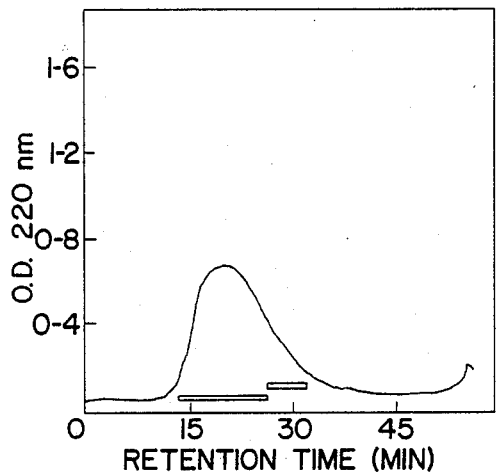

A similar chromatogram is shown in FIG. 4, a preparative run for bovine albumin.

FIG. 5 shows a combination of FIGS. 1 and 2 and illustrates excellent separation of insulin, albumin and $\beta$-lactoglobulin A and B.

FIG. 6 illustrates that fine tuning leads to separation of the $\beta$-lactoglobulins.

Figure 7:
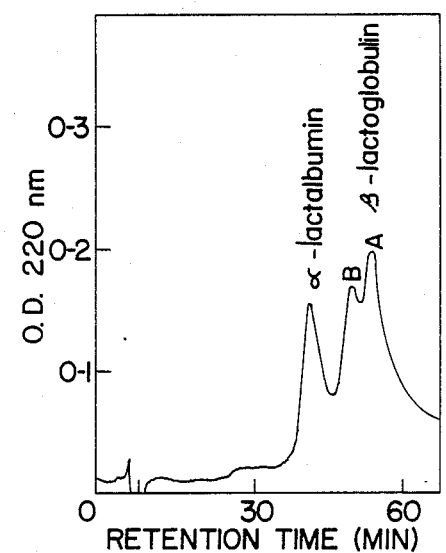

FIG. 7 shows clear separation of whey protein components.

Figure 8A:
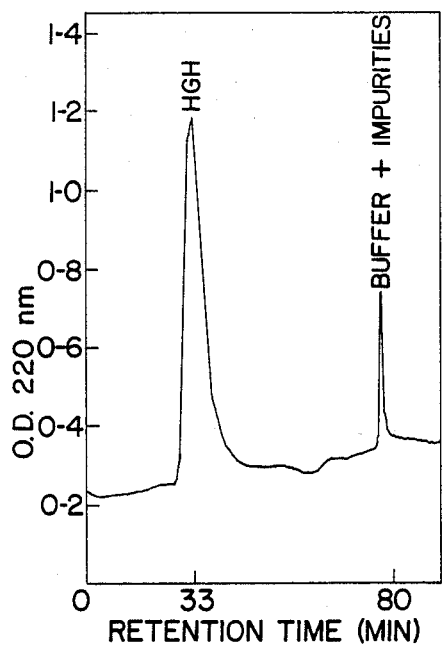

FIG. 8a shows how a commercial sample of human growth (HGH) can be clearly separated from several very minor contaminants.

Figure 8B:
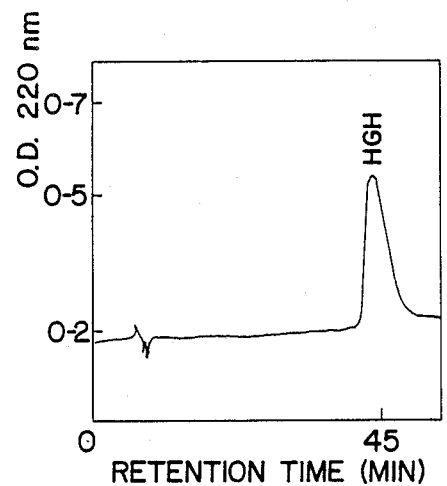

FIG. 8B illustrates a sample of HGH from a source in New Zealand.

EXAMPLE 5: Coating of the Column with Acid Added to Mobile Phase

In passing a buffer system through a column, it is assumed that part of the buffer components are "bound" to the column. This could be permanently or in a dynamic equilibrium. It is believed that the binding of the buffer to the reversed phase column results in the deactivation of silanol groups with the consequent improvement in the chromatography of proteins. The occurrence of this interaction is demonstrated in a new Rad Pak-$C_{18}$ column (Waters: 8MBC1810$\mu$ P4194A01) which was washed with methanol and 80% isopropanol and a gradient set up to 10% isopropanol. In an isocratic system using 10% isopropanol/water 20 microliter of a 1% solution of citric acid dissolved in the same solvent was injected repeatedly. The peak (detection RI) was trapped and the sample titrated with 0.01M sodium hydroxide. On the first injection the acid peak was wider than in all following injections (see FIG. 9 and Table 3). A small quantity of the acid had been bound to the column. Normally titration of the peak took 0.80 ml of sodium hydroxide. For the first peak however 0.60 ml was needed.

It seems that a certain amount of acid is bound during the first injection (equivalent of ~1 -2 $\mu$Mol) also the peak shape shows that interaction between the column and the citric acid has occurred.

The fact that after thorough washing, the column absorbed a similar amount of acid again on repeating the experiment suggests that much of the acid is not irreversibly bound to the column but is in a dynamic equilibrium with it.

With another column, NovaPak-$C_{18}$ (Waters; 8NVC18 5 micron: P4136DO1), the experiment was repeated. Again, we observed the phenomenon described above (FIG. 10).

TABLE 3

| | Quantity of 0.01 M Sodium Hydroxide Needed in Titration (ml) | | | |
|---|---|---|---|---|
| | 1 | 2 | 3 | 4 |
| COLUMN 8MBC18 10 micron PEAK | | | | |
| Experiment 1: citric acid | 0.15 | 0.25 | 0.30 | 0.30 |
| COLUMN 8NVC18 5 micron | | | | |
| Experiment 2: citric acid | 0.20 | 0.30 | 0.30 | 0.30 |

EXAMPLE 6: RECOVERY OF PROTEINS FROM THE REVERSED PHASE COLUMN

The recovery of a protein from a column depends strongly on the way the chromatographic process is carried out.

If bovine serum albumin (BSA) is injected at 0% organic solvent, the BSA is usually eluted at about 50% organic. The recovery can be very small even down to 10%.

If, however BSA is injected at a higher level of organic solvent (25%) and the gradient started, it will elute at a lower percentage of organic solvent than mentioned before and the recovery improves considerably and may reach 95% or more. To ensure the best possible separation and recovery the following scheme can be used:

1. Find out the maximum percentage of organic solvent in which the protein shows retention in 5% steps. For example, if BSA shows no retention at all in 30% organic then start the chromatography at 25%.

2. Set up a shallow gradient up to the lowest possible percentage of organic solvent that will elute the protein(s). Examples; (A) Separation of bovine and porcine insulin. Usually run in 1 hour from 15-25% buffer B (containing 0.1% acid +1% salt in water/isopropanol 1:4).

(B) Separation of $\alpha$-lactalbumin, $\beta$-lactoglobulin A and B. Usually run from 25-50% buffer B in 1 hour.

If a mixture of proteins with wide ranging polarities is injected the recoveries may vary considerably, unless the selection of the mobile phase and gradient condition is carefully made.

EXAMPLE 7: COMPARISON OF DIFFERENT COLUMNS FOR PROTEIN SEPARATION

From the results of the twenty analytical columns tested with different solvent systems, it is clear that only the very wide pore packings are suitable for high MW protein separations. (See Table 4 for column parameters). In general, the best separations are obtained on the Supelco LC-38 and Vydac C-4 columns (both 300Å).

A column that performs very well for the chromatography of the different insulins (Water Assoc. NOVA-PAK C18) is less successful with the bigger proteins like BSA, because of its small pores 10 nm (approximately 100Å).

The 250 mm columns like the Whatman Protesil - 300 OCTYL25 and Synchropak RP-P (CR 103-25) give rise to fairly high back pressures and are therefor not ideal with solvent systems of high viscosity.

In conclusion, it may be said that an ideal column for analytical protein separations in the system described is short (50 or at the most 100 mm long) and has a pore size of approximately 30 nm (300 Å).

For preparative liquid chromatography of proteins longer columns will be needed but since they will also be wider, no problems are expected with back pressures.

TABLE 4

PROPERTIES OF REVERSED PHASE COLUMNS

| Column | Particle Shape | Particle Size μ | Surface Area m²/g | Organic Loading C. w/w % | Pore Size Å | Capped Capped |
|---|---|---|---|---|---|---|
| Supelco LC-3DP | s* | 5 | 140 | 4.4 | 300 | + |
| Supelco LC-318 | s | 5 | 140 | 10 | 300 | + |
| Vydac C4 | i** | 5 | 100 | 4 | 330 | |
| NovaPak C18 | s | 4 | — | 7 | 50 | + |
| Rade-Nova-Pak-C18 | s | 5 | — | 7 | 50 | + |
| Rad Pak C18 | s | 10 | 200 | 11 | 90 | — |
| Protesil-octyl | i | 10 | 200 | 7.5 | 300 | + |

*s = spherical
**i = irregular (A) General protein separation (FIG. 11 citric acid)
Normally a mixture was injected containing:
| | |
|---|---|
| insulin (porcine) | peak 1 |
| cytochrome C (horse heart) | 2 |
| bovine serum albumin | 3 |
| α-lactalbumin | 4 |
| myoglobin (equine skeletal muscle) | 5 (+8) |
| β-lactoglobulin B | 6 |
| and β-lactoglobulin A | 7 |

(B) Separation of β-lactoglobulin A and B (FIG. 12 citric acid)
A mixture of proteins isolated from whey was injected containing:
| | |
|---|---|
| α-lactalbumin | peak 4 |
| β-lactoglobulin B | 6 |
| β-lactoglobulin A | 7 |

(C) Separation of Different Insulins (FIG. 13 citric acid)
A mixture of bovine and porcine insulin was used to test the columns. When the separation was very good also equine insulin was injected.
Peak (a) equine insulin A chain Ala$_8$—Ser—Val
(b) bovine insulin A chain Thr$_8$—Ser—Ile
(c) porcine insulin A chain Thr$_8$—Gly—Ile

EXAMPLE 8: PREPARATIVE CHROMATOGRAPHY OF 1.0 GRAM OF BOVINE SERUM ALBUMIN (citric acid + salt)

Instrument: Prep LC/System 500A (Waters)
Detection: 280 nm A 2.0
Buffer A: 0.1% citric acid +1% NaCl in H$_2$O/95%-EtOH 75:25
Buffer B: 0.1% citric acid +1% NaCl in H$_2$O/95%-EtOH 45:55

1.0 g of BSA dissolved in 200 ml buffer A was pumped onto the column (1 column C18 - silica 250×55 mm, Waters) followed by another 100 ml of buffer A.

A concave gradient was now started using 1 liter of buffer A and 5 liters of buffer B.

Figure 14:
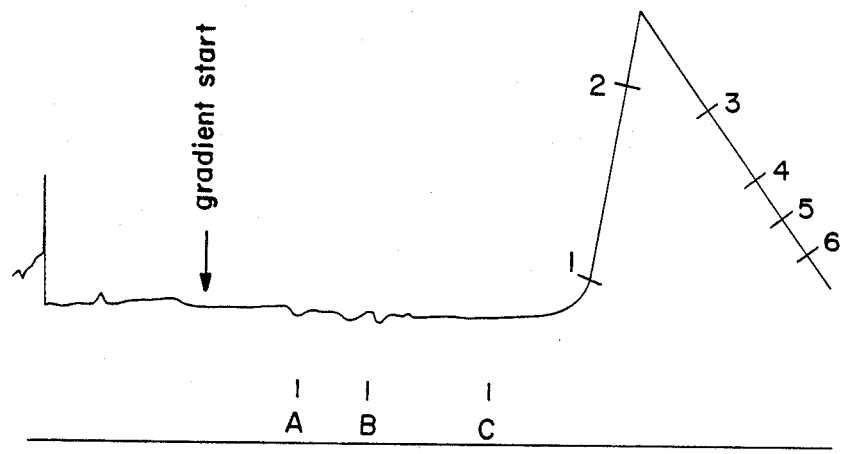
Figure 15B:
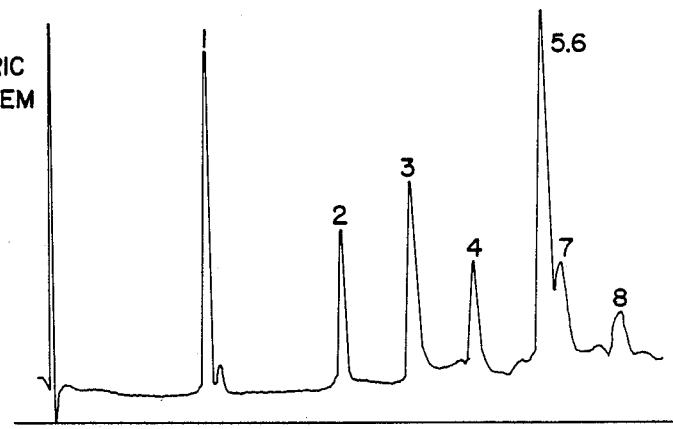
Figure 15C:
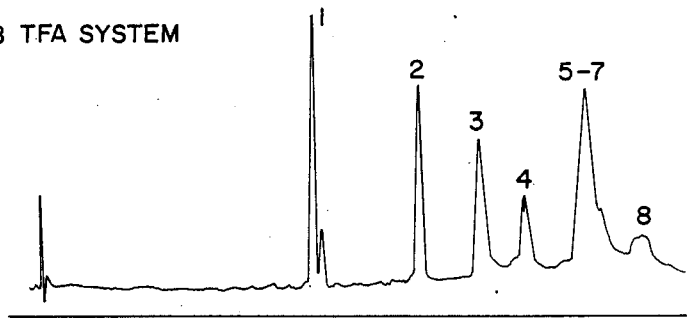

The peak was trapped in several fractions. (FIG. 14). Recovery 98–100%.

EXAMPLE 9: COMPARISON OF CITRIC ACID WITH PHOSPHORIC ACID AND TRIFLUOROACETIC ACID

In a final number of experiments, we have compared the systems of this invention with the known phosphoric acid and TFA systems.

In FIGS. 15 and 16, it is demonstrated that the weaker acid gives more resolution than the stronger acid or in other words the resolving power of citric acid > phosphoric acid > TFA >.

EXAMPLE 10: AUTOMATED PREPARATIVE CHROMATOGRAPHY OF PROTEINS ON WIDE PORE C-18 SILICA

Column
A column was packed with Synchroprep a C18-silica, spherical, 30 with 300 Å pores. Column dimensions 250×10 mm φ. A number of automatic purifications of proteins were carried out.

Buffers
(A) 0.1% citric acid + 1% sodium chloride in water/95%-ethanol 9:1.
(B) 0.1% citric acid + 1% sodium chloride in water/95%-ethanol 1:4.

EXAMPLE 10A: HUMAN SERUM ALBUMIN

Repeatedly charges of 50 mg of HSA were injected and a linear gradient started from 45 to 55% B over 20 minutes at 1.5 ml/min. The first peak is a mixture of citric acid added to the sample and N-acetyltryptophan, present in the sample as a stabilizer. The second peak is albumin. Arrows indicate where trapping was started and ended.

After 30 minutes, the buffer mixture was changed back to initial conditions. (The difference between starting and final conditions is small enough that this can be done without running a gradient).

For 10 minutes, the column was run at initial conditions, then a new sample injected and the gradient started 2 minutes later.

EXAMPLE 10B: BOVINE SERUM ALBUMIN

BSA (40 mg) was injected repeatedly. The procedure was as in example 11A but the gradient used was from 50–60% B at 1.5 ml. min. in 15 minutes. An abrupt change to initial conditions was possible after 30 minutes.

After a number of runs, a gradient was run up to 100% B to clean the column (fraction B).

EXAMPLE 10C: BOVINE INSULIN

Figure 17B:
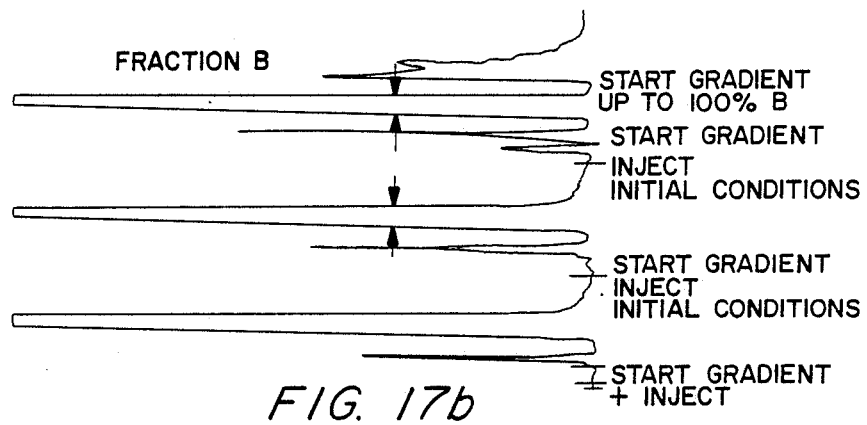
Figure 17C:
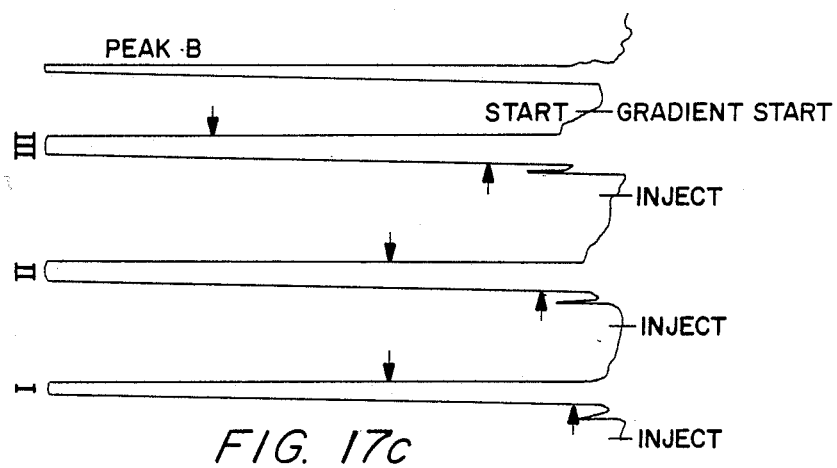

An isocratic system was employed at 45% B which made gradients unnecessary. FIG. 17B shows a simulated automatic run where insulin was injected every 36 minutes.

In this run, the quantities injected were increased from 5 mg (run not shown) up to 40 mg (peak III). Later, a gradient was run up to 100% B to clean the column whereby Peak B was eluted (not identified).

CHROMATOGRAMS: See FIG. 17.

Sample Preparation

Retention times of the proteins are influenced when relatively large quantities are injected. Preferably, the proteins are dissolved in the same solvent in which the column is equilibrated. In the case of insulin, this is possible if enough solid citric acid is added to the mixture.

In the case of the albumins, this was not possible.

To dissolve albumin in a high concentration 20 or 25 mg/ml in a solvent containing 45 or 50%, 95% ethanol is not possible. However, a smaller amount of isopropanol can replace the ethanol without significantly altering the polarity of the sample solvent.

Human Serum Albumin 1 ml of albumin (a 25% solution of HSA) was diluted with 7 ml of buffer A, then 2 ml of isopropanol added and solid citric acid to pH 3.0.

Bovine Serum Albumin

BSA (200 mg, Sigma) was dissolved in 8 ml buffer A, 2 ml of isopropanol added and solid citric acid to pH 3.0.

Insulin (200 mg Nordisk) was suspended in 10 ml of a mixture of 45% buffer B and 55% buffer A. Solid citric acid was added until all insulin was dissolved.

EXAMPLE 11: SEPARATION OF PROTEINS USING MALONIC ACID GLUCURONIC ACID AND FORMIC ACID

Reversed phase columns used for this work were the Supelco LC-318 and the Vydac Protein-C4 as examples of wide pore (300Å) columns and the Waters Novapak C18 and 8NVC18 5μ as examples of narrow pore C18-silicas.

The buffer systems were:

Buffer A: 0.1% acid +1% NaCl in water/isopropanol 9:1

Buffer B: 0.1% acid +1% NaCl in water/isopropanol 1:4

Samples (1) (FIG. 18) The general protein mixture described in relation to FIG. 11.

(2) (FIG. 19) The mixture of whey proteins described in relation to FIG. 12.

(3) (FIG. 20) Insulins; equine, bovine and porcine.

Results (a) As demonstrated before the wide pore columns are superior for protein work.

(b) The resolution improves when the acid is weaker or in other words, formic acid is better than glucuronic, glucuronic is better than malonic.

(c) Careful comparison of these results with those obtained with citric acid shows that formic acid is certainly a good acid for this work coming close to the resolving power of citric acid. From a health point of view, formic acid, however, may not be used for preparative h.p.l.c. of proteins to be used in medicine.

EXAMPLE 12: SALTS IN BUFFER

It has been shown in many of the previous examples that the addition of from about 0.5 to 2.0% salt enhanced the resolution. Satisfactory salts are set out in Table 5.

TABLE 5

| SALTS | REMARKS |
|---|---|
| sodium chloride | good |
| potassium chloride | good |
| ammonium chloride | good |
| lithium chloride | moderate |
| ammonium sulphate | unsatisfactory |
| sodium sulphate | unsatisfactory |
| guanidine hydrochloride | good |

Instead of salts, neutral, non-ionic compounds were added to the mobile phase. For example, urea, glucose and glycerol were tried but did not produce useful separations.

EXAMPLE 13

A sample of recombinant human growth hormone (rhGH) and a sample of met. human growth hormone (met.hGH) were partially purified from their reaction mixture using the techniques of ion exchange, gel filtration and hydrophobic interaction chromatography. The partially purified recombinant proteins were then passed through reversed phase columns using Synchroprep-RP-P as the support. Synchroprep-RP-P is a spherical $C_{18}$-silica of 30 mg sphere size with 300 Å pores, from Synchrochrome Inc. The buffer system employed are set out in the description of FIG. 21 above.

System 4 is the biologically acceptable one. Systems 1, 2, 3, were used for comparison. The peaks show that in all cases, the separation of the recombinant protein is reasonably good. The mobile phase in system is physiologically acceptable and this system can be used for producing pharmaceutical grade products.

EXAMPLE 14

Figure 23:
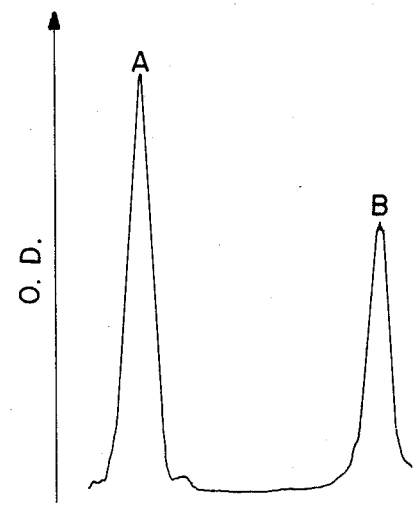

The column and buffer system used for this system are described with reference to the short description of FIG. 23 above. The peak lettered "A" is that from the buffer components while the peak "B" is that from the recombinant human insulin.

This illustrates that the recombinant human insulin was not denatured when passed through a preparative scale.

We claim:

1. A method of purifying on a preparative scale a recombinant deoxyribonucleic acid protein derived from a mixture thereof with cell proteins by reversed phase HPLC, which comprises the steps of:
    providing a column packed with an HPLC support of sufficient porosity to allow passage of proteins therethrough,
    introducing a recombinant deoxyribonucleic acid protein derived from mixture thereof with cell proteins into the end of said column, and
    eluting said column with a mobile phase comprising substantially pure water containing 0.005 to 1 molar of a physiologically acceptable carboxylic acid, the acid being of the general formula YCOOH wherein Y is a polar electron withdrawing group capable of hydrogen bonding silanol groups in a silicarbonaceous support, said solution also containing from 10.5% up to 95% by volume of a physiologically acceptable organic solvent.

2. A method as claimed in claim 1 wherein said physiologically acceptable carboxylic acid is citric acid and said organic solvent is ethanol.

3. A method as claimed in claim 2 which includes the subsequent step of isolating said recombinant protein by a method selected from the group consisting of ultrafiltration and dialysis.

4. A method as claimed in claim 1 wherein said recombinant protein is selected from the group consisting of recombinant human growth hormone and recombinant human insulin.

* * * * *